United States Patent
Wagner et al.

(10) Patent No.: US 7,803,610 B2
(45) Date of Patent: Sep. 28, 2010

(54) METHOD, APPARATUS AND SYSTEM FOR SEPARATING EUCARYOTIC OR PROCARYOTIC CELLS OR OTHER PARTICULARLY BIOLOGICAL MATERIAL FROM A SUSPENSION

(75) Inventors: Roland Wagner, Vechelde (DE); Ahmed Elsayed Elsayed, Braunschweig (DE)

(73) Assignee: GBF mbH, Braunschweig (DE)

( * ) Notice: Subject to any disclaimer, the term of this patent is extended or adjusted under 35 U.S.C. 154(b) by 1072 days.

(21) Appl. No.: 10/556,305

(22) PCT Filed: May 10, 2004

(86) PCT No.: PCT/EP2004/004976

§ 371 (c)(1), (2), (4) Date: Aug. 22, 2006

(87) PCT Pub. No.: WO2004/099362

PCT Pub. Date: Nov. 18, 2004

(65) Prior Publication Data

US 2007/0039855 A1    Feb. 22, 2007

(30) Foreign Application Priority Data

May 9, 2003 (EP) .................... 03009784

(51) Int. Cl.
- C12N 1/02 (2006.01)
- C12N 5/07 (2006.01)
- C12N 5/10 (2006.01)
- C12N 5/071 (2006.01)
- C12N 5/02 (2006.01)
- C12N 5/00 (2006.01)
- C12M 1/00 (2006.01)
- C12M 3/00 (2006.01)

(52) U.S. Cl. ............... 435/308.1; 435/283.1; 435/348; 435/366; 435/374; 435/261

(58) Field of Classification Search ............... 435/261, 435/283.1, 308.1, 348, 366, 374
See application file for complete search history.

(56) References Cited

U.S. PATENT DOCUMENTS

| 4,134,827 | A | * | 1/1979 | Frykhult | .............. 209/734 |
| 4,259,180 | A | * | 3/1981 | Surakka et al. | .......... 209/732 |

FOREIGN PATENT DOCUMENTS

| EP | 1280885 | 2/2003 |
| WO | WO/01/85902 | 11/2001 |

* cited by examiner

*Primary Examiner* — Walter D Griffin
*Assistant Examiner* — Lydia Edwards
(74) *Attorney, Agent, or Firm* — Pearl Cohen Zedek Latzer, LLP; Mark S. Cohen

(57) ABSTRACT

A method for separating eucaryotic or procaryotic cells or other particularly biological material which is sensitive against high shearing forces from a suspension is provided using at least one hydrocyclone with an inlet and an outlet. The outlet of the hydrocyclone is essentially opposite to the inlet and the interior space of the hydrocyclone converges towards the outlet. The suspension is delivered to the inlet of the hydrocyclone, and the suspension enriched with the cells is drained off from the outlet. The enriched suspension is then guided from or through the outlet by a flow means in such a way, that a minimum of shearing stresses occurs and the kinetic energy of the enriched suspension at the outlet of the hydrocyclone is reduced that the viability of the cell material is influenced at a minimum.

30 Claims, 5 Drawing Sheets

METHOD, APPARATUS AND SYSTEM FOR SEPARATING EUCARYOTIC OR PROCARYOTIC CELLS OR OTHER PARTICULARLY BIOLOGICAL MATERIAL FROM A SUSPENSION

CROSS-REFERENCE TO RELATED APPLICATIONS

This application is a National Phase Application of PCT International Application No. PCT/EP2004/004796, International Filing Date May 10, 2004, claiming priority of EP Patent Applications, 03009784.4, filed May 9, 2003, each of which being incorporated by reference herein in their entirety.

FIELD OF THE INVENTION

The present invention relates to a method, apparatus and system for separating eucaryotic or procaryotic cells or other particularly biological material, which is sensitive against high shearing forces/stresses, from a suspension.

BACKGROUND OF THE INVENTION

In EP 1 280 885 A1 the separation of mammalian cells, insect cells and botanical cells from cell suspension is achieved by using a hydrocyclone.

The typical hydrocyclone described therein consists of a tapered part/cone and an upper cylindrical part, which comprises an inlet for tangential feed in the suspension. The cylindrical part is closed by a top, which comprises in the middle an opening at the top, the overflow. The cone of the hydrocyclone ends with an outlet, the underflow. The hydrocyclone has no moving parts, it operates automatically and it has a long durability. The conventionally domain for using hydrocyclones is to concentrate suspensions, wherein coarse grained drain off the device in form of concentrated suspension at the underflow of the hydrocyclone. The fine particles, which are not separated, leave the hydrocyclone in form of a diluted suspension at the opening at the top of the apparatus, the overflow.

The initial suspension is fed tangentially into the inlet of the hydrocyclone, which is generally at the cylindrical part of the hydrocyclone. The suspension starts to spin within the hydrocyclone. As the suspension begins to move down the tapered section of the hydrocyclone, it accelerates. The cell material, having typically a higher density than the rest of the suspension, moves to the outside wall and leaves the hydrocyclone through the outlet at the underflow. The rest of the suspension is recovered through the opening at the top of the hydrocyclone.

In EP 1 280 885 A1 a hydrocyclone is used in a perfusion system wherein the repatriated cell material leaves the underflow of the hydrocyclone uncontrolled into the bioreactor/collection vessel. The cell material bounces with the maximum velocity onto the surface of the suspension inside the bioreactor. This may lead to high and unphysiological shearing stresses/forces, which can affect the viability and the productivity of the cells negatively.

It may also occur that a sudden decrease of pressure resulting in a sudden expansion/relaxation at the end of the outlet/underflow of the hydrocyclone or a large pressure difference between the inlet and the outlet affects the viability of the cell material negatively. Due to the sudden pressure decrease by emitting the suspension of the underflow back to the suspension in the bioreactor causes high shearing forces to the sensitive cell material, which are responsible for degrade the viability of the cells.

SUMMARY OF THE INVENTION

It is therefore an object of the present invention to provide a method, an apparatus and/or a system which controls the outflow of the cell enriched suspension in such a way, that only small shearing stresses appear and the viability of the cell material is held on a high level.

This object is solved with the features of the claims.

The invention proceeds from the basic idea to use a hydrocyclone for the separation of eucaryotic or procaryotic cells or other particularly biological material and guide and/or decelerate the cell material enriched suspension from or through the outlet of the hydrocyclone in such a way, that a minimum of shearing stresses occurs and the kinetic energy of the enriched suspension at the outlet of the hydrocyclone is reduced that the viability of the cell material is influenced at a minimum.

In principle, a high pressure difference is desired for high enrichments which results in higher rotational speed in the tapered part of the hydrocyclone and higher kinetic energy at the outlet of the device. This represents a problem for said cell material as the rotational speed at the outlet of the hydrocyclone could bear high shearing forces to the cell material, which could be damaged and decrease the viability of the cell material in the suspension. There are in principle two effects which should be considered for a careful treatment of the cell material guiding from the outlet of the hydrocyclone into the bioreactor:

1. The cell enriched suspension can slowed down by a flow means which is applied at the underflow of the hydrocyclone. The flow means could be preferably a rigid or flexible tube being connected to the outlet at the underflow of the hydrocyclone. The rotational motion of the cell enriched suspension at the outlet of the hydrocyclone is smoothly transformed into a laminar flow inside the flow means. The flow means at the outlet of the hydrocyclone is preferably applied in a first acute angle towards the longitudinal axis of the outlet or the longitudinal axis of the hydrocyclone. The cell material decelerates in the flow means avoiding high shearing stresses due to the tangential flushing of the flow means. The length of the flow means is preferably greater than 10 cm and more preferably between 50 and 100 cm to slow down the suspension. This effect should be considered when a direct dunking of the flow means inside the suspension of the bioreactor is not possible or desired as for systems, wherein the hydrocyclone is applied in an external loop of the bioreactor. This setup is favorable for the process development with small bioreactors like benchtop bioreactors.

2. Beside slowing down the suspension in the flow means, also the drain off back to the bioreactor could cause high sheering stresses. Therefore alternatively or additionally a guiding direct or by a flow means into the suspension, under the upper level of the fluid inside the bioreactor is performed. The outlet of the hydrocyclone could be dunked down directly into the fluid of the bioreactor or the hydrocyclone is applied above the upper level of the fluid of the bioreactor and the enriched suspension is guided from the outlet of the hydrocyclone into the bioreactor by a flow means. The flow means, preferably a rigid or flexible tube, guides the suspension from the outlet of the hydrocyclone into the fluid wherein the end of the flow means opposite to the outlet of the hydrocyclone guides the suspension under the upper level of the fluid of the bioreactor. The latter method is preferably as the power of separation of the hydrocyclone is dependent on the hydrostatical pressure. For hydrocyclones applied above the fluid level of the bioreactor, a higher hydrostatical pressure is achieved and therefore a larger volume which could be perfused by time unit. In this case the friction of the cell material with the molecules of the suspension/fluid in the bioreactor decelerates the cell material and prevents damage of said cell material.

Another alternative possibility which may optionally be combined with one or both of the before mentioned solutions is the drain off the suspension above (or below) the upper fluid level of the bioreactor by a flow means against the wall of the bioreactor or a separate container. The flow means, preferably a tube with round diameter, is arranged at its distal end in a second acute angle to the wall of the bioreactor. The distal end of the flow means, opposite to the outlet of the hydrocyclone, is preferably cut in a third acute angle with reference to the longitudinal axis of the flow means preferably corresponding to the before mentioned second acute angle. Therefore the tube opening at the distal end is ovally shaped. The ovally shaped opening of the flow means is preferably applied at a small distance from the wall of the bioreactor, so that the cell material suspension flows substantially tangential against the wall. The cell material suspension flows vertically down the wall, but the flow direction may also differ from the vertical direction.

This separation method is not only applicable for perfusion systems, rather it can be used in general for any separation of eucaryotic or procaryotic cells which is sensitive against high shearing forces wherein a high viability is desired.

BRIEF DESCRIPTION OF THE DRAWINGS

In the following the invention will be explained in more detail in cunjunction with appended drawings, wherein.

DETAILED DESCRIPTION

Figure 1:
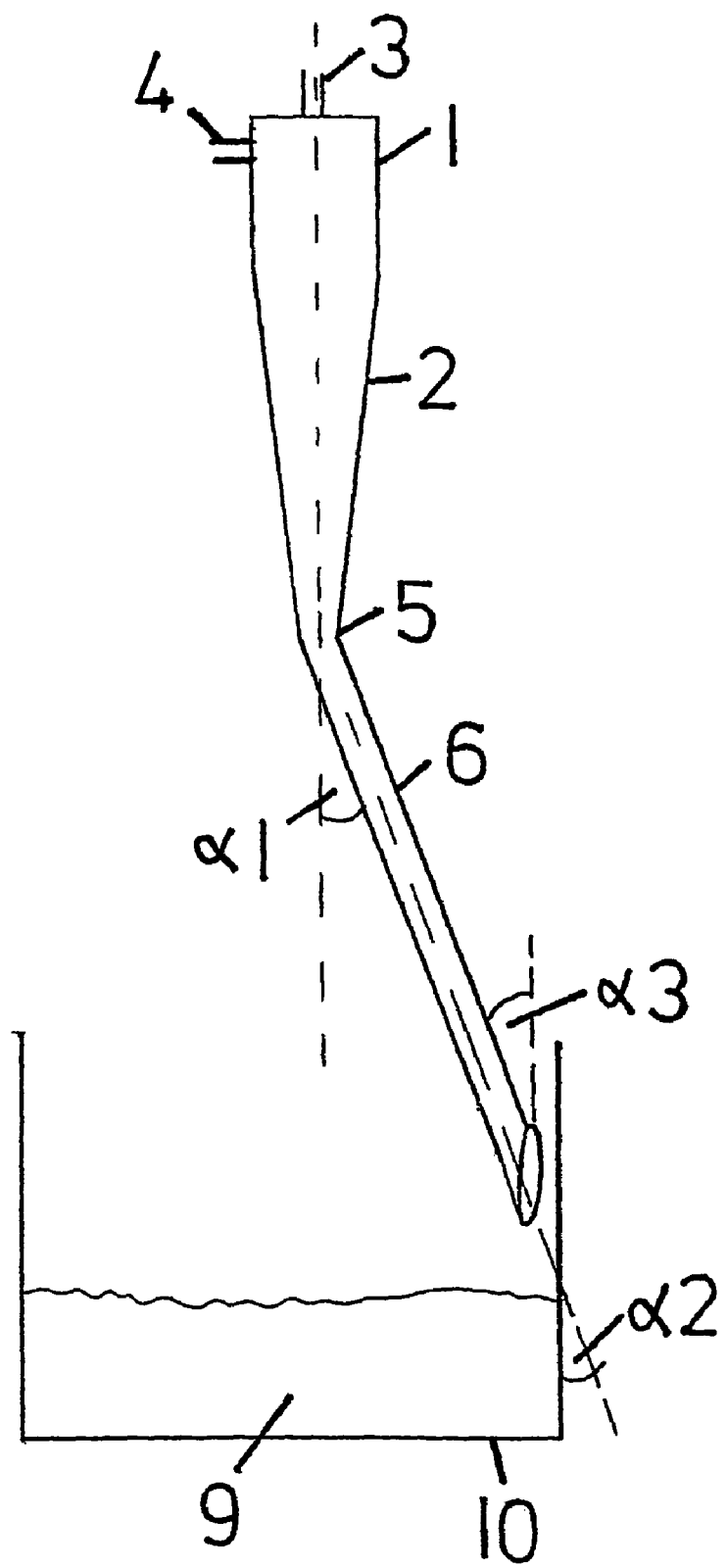
FIG. 1 shows a first preferred embodiment of present invention with a flow means in an acute angle.

FIG. 1 shows the first preferred embodiment of present invention for separating eucaryotic or procaryotic cells or other particularly biological material comprises at least one hydrocyclone with at least an inlet 4 and an outlet 5. The outlet 5 forming the underflow of the hydrocyclone is essentially opposite to the inlet 4. The interior space 2 of the hydrocyclone converges towards the outlet 5. The suspension enters the hydrocyclone through the inlet 4 disposed tangentially to the interior wall of a longitudinally extending separation chamber 1, which is applied above the tapered formed chamber 2. The inlet pressure creates a high inlet velocity which in turn sets up a free liquid vortex within the chamber. Centrifugal forces act on the liquid and the cell material of the suspension resulting in a separation based on their relative densities. The hydrocyclone will have at least two outlets from the separation chamber, said outlet 5 being positioned essentially opposite to the inlet to accommodate the underflow 5 of the higher density fraction, and a second being positioned at the top end of the hydrocyclone to accommodate an overflow 3 of the less density fraction. The cell enriched suspension has a high rotational speed and therefore the cells have a high kinetic energy at the outlet 5. According to the invention the cell material should at or after the outlet decelerate that only small shearing forces occur on the cell material. This can be achieved by a flow means 6 attached to the outlet of the hydrocyclone. In this preferred embodiment the flow means 6 is arranged in an essentially first acute angle $\alpha 1$ towards the longitudinal axis of the outlet or the longitudinal axis of the hydrocyclone applied, so that the enriched suspension at least close to the outlet has an essential tangential flow within the flow means. The flow means 6 can be a flexible or rigid tube. Attaching a flow means in an essentially acute angle $\alpha 1$ towards the longitudinal axis of the outlet or the longitudinal axis of the hydrocyclone results in an ovally shaped hole at the outlet of the hydrocyclone. To reduce the kinetic energy of the cell material before dropping back into the bioreactor 10 the flow means 6 has a preferred minimum length of at least 10 cm more preferably a length between 50 and 100 cm.

For using the hydrocyclone for example in a perfusion system, the flow means 6 guides the suspension back into the bioreactor. To drain off the suspension above the upper level of fluid 9 in the bioreactor 10 the flow means 6 is applied in a second acute angle $\alpha 2$ against the wall of the bioreactor. The end of the flow means, opposite to the outlet of the hydrocyclone, is preferably cut in a third acute angle $\alpha 3$. Therefore the intersection or opening at the distal end of the tube is shaped ovally. The ovally shaped opening at the distal end of the flow means is arranged in a small distance facing the wall of the bioreactor, so that the cell material flows substantially tangential against the wall. This distance is preferably in the range of 1 to 50 mm.

Figure 2:
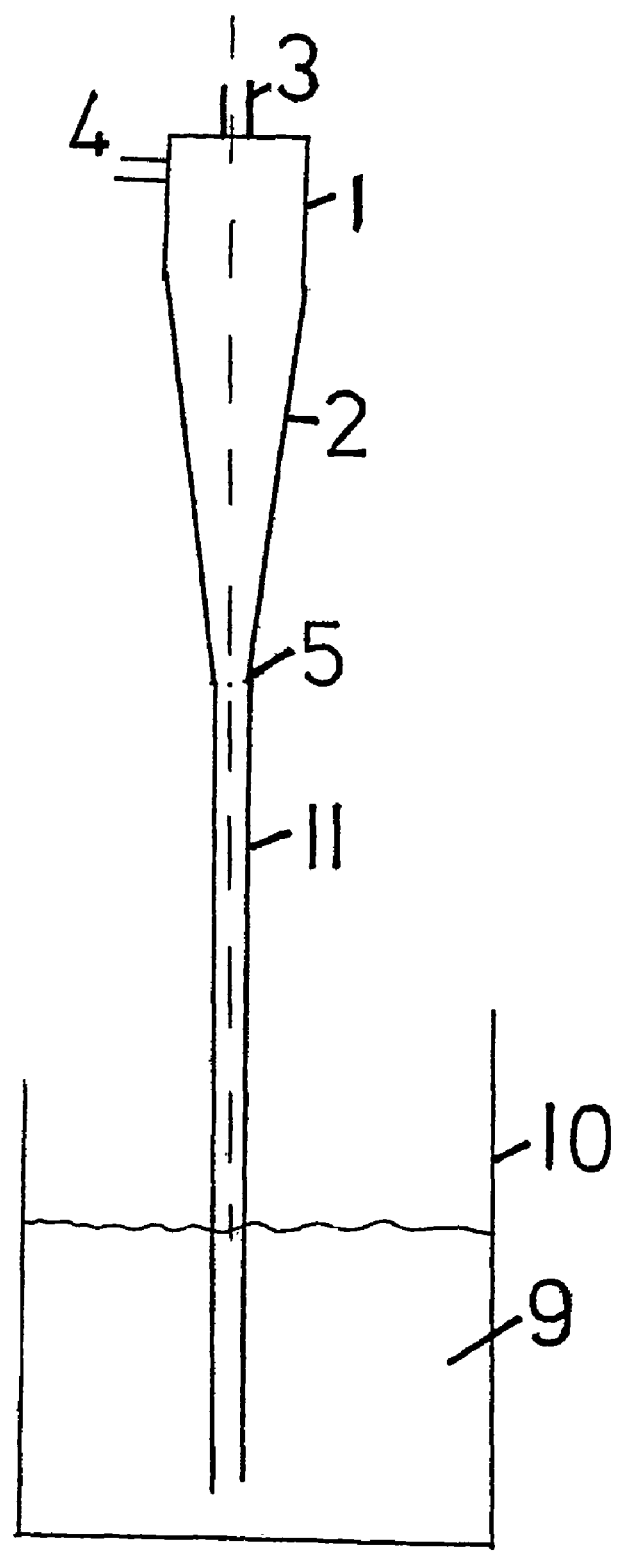
FIG. 2 shows a second preferred embodiment of present invention with a flow means guiding the suspension under the upper level of the fluid in the bioreactor.

The second preferred embodiment of the present invention, shown in FIG. 2 provides a hydrocyclone connected by a flow means 11 or a communicating flange to the bioreactor 10 wherein the outlet 5 of the hydrocyclone is arranged relative to the bioreactor so that the suspension is submitted below the upper level of the suspension/fluid inside the bioreactor. The flow means 11 of the bioreactor is dunking into the fluid 9 of the bioreactor 10 so that the suspension from the flow means is transported below the upper level of the fluid 9 within the bioreactor. Due to the dunking in of the flow means the hydrostatic pressure inside the hydrocyclone is small enough to avoid kinetic energies that could damage the cell material. Furthermore, the cell material is decelerated due to the friction with the molecules of the suspension.

On one hand, the shearing stresses are reduced when reducing the hydrostatic pressure, otherwise the separation power is reduced. For desired higher production rates, the use of at least two hydrocyclones in parallel of serial or combination of parallel and serial is favourable.

Figure 3:
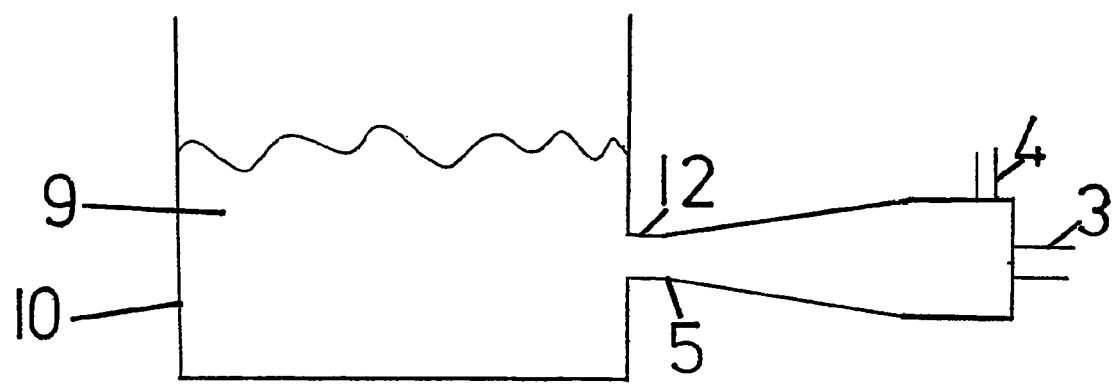
FIG. 3 shows a third preferred embodiment of present invention, guiding the suspension directly under the upper level of the fluid in the bioreactor.

In FIG. 3, the hydrocyclone guides the cell enriched suspension through the socket 12 below the upper level of the fluid 9 of the bioreactor 10, wherein the hydrocyclone is arranged horizontal. It is also appreciated to arrange the hydrocyclone vertically or in any other angle to the bioreactor.

For pilot installations or production constructions the hydrocyclone could be applied with a screw thread DN25 with O-ring seal which could be connected with a corresponding bioreactor connecting piece with the top of the bioreactor. This connection could be sterile so that an in situ sterilisation of the hydrocyclone is possible. For bioreactors lager than 250 liter volume the use of multiple hydrocyclones is preferred which could end in one common flow conduit.

In case of parallel use of two or more hydrocyclones, the outlets of a plurality of hydrocyclones could end in a common flow conduit for example.

It is apparent that the above disclosed solutions shown in FIGS. 1 to 3 and its features may be combined at least in part. For example the embodiment shown in FIG. 2 may comprise a flow means 11 which is arranged at an acute angle with reference to the hydrocyclone and/or the wall of the bioreactor. Moreover, the hydrocyclone with the straight flow means 11 as shown in FIG. 2 may be provided as shown in FIG. 1, wherein the distal end of the flow means shortly ends before the wall of the bioreactor either above or below the surface of the fluid.

Figure 4:
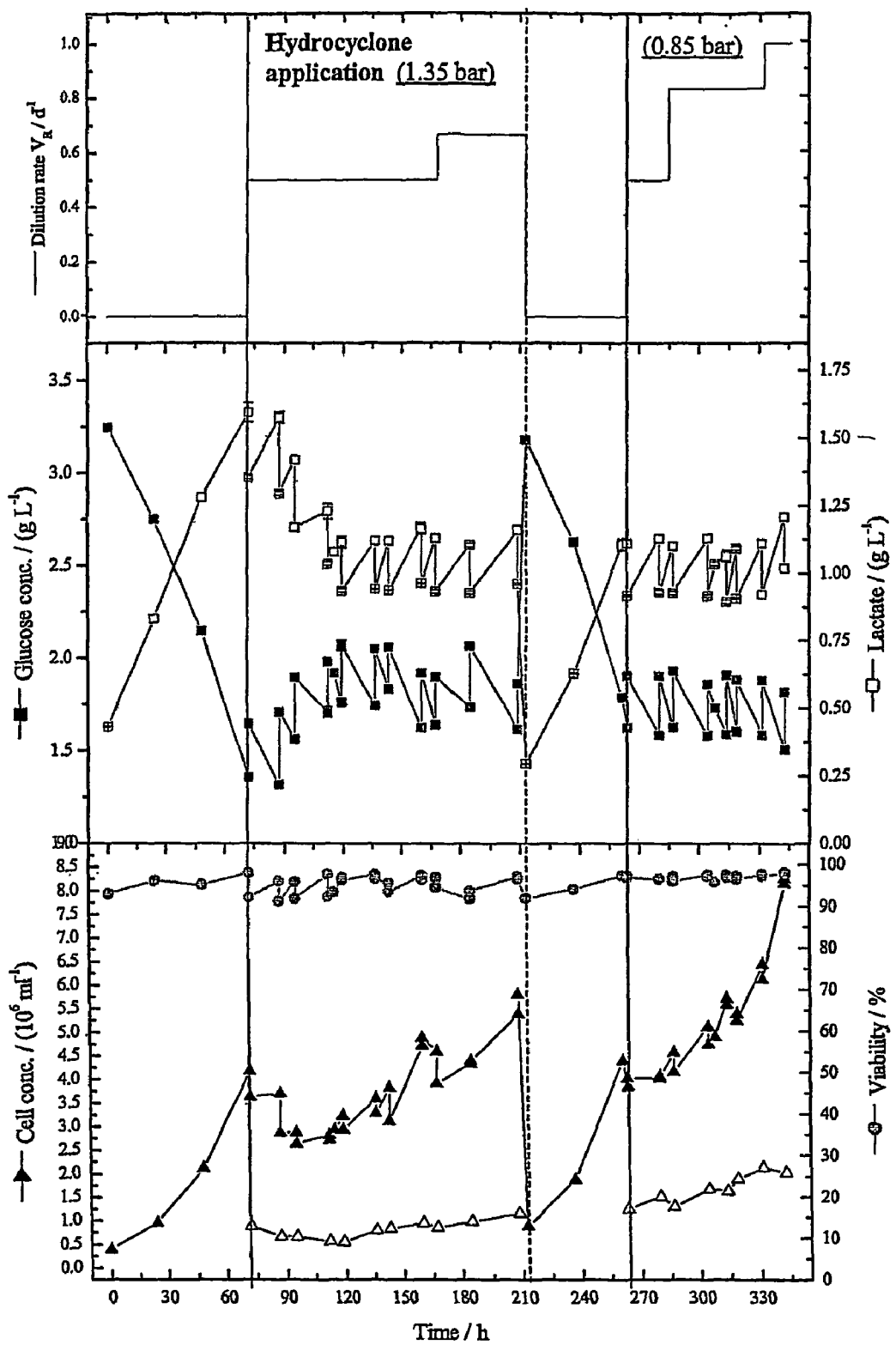
FIG. 4 is an example with a continuous cultivation of SP2/0 excells in a 5 L reactor by hydrocyclone perfusion in accordance with the present invention.
Figure 5:
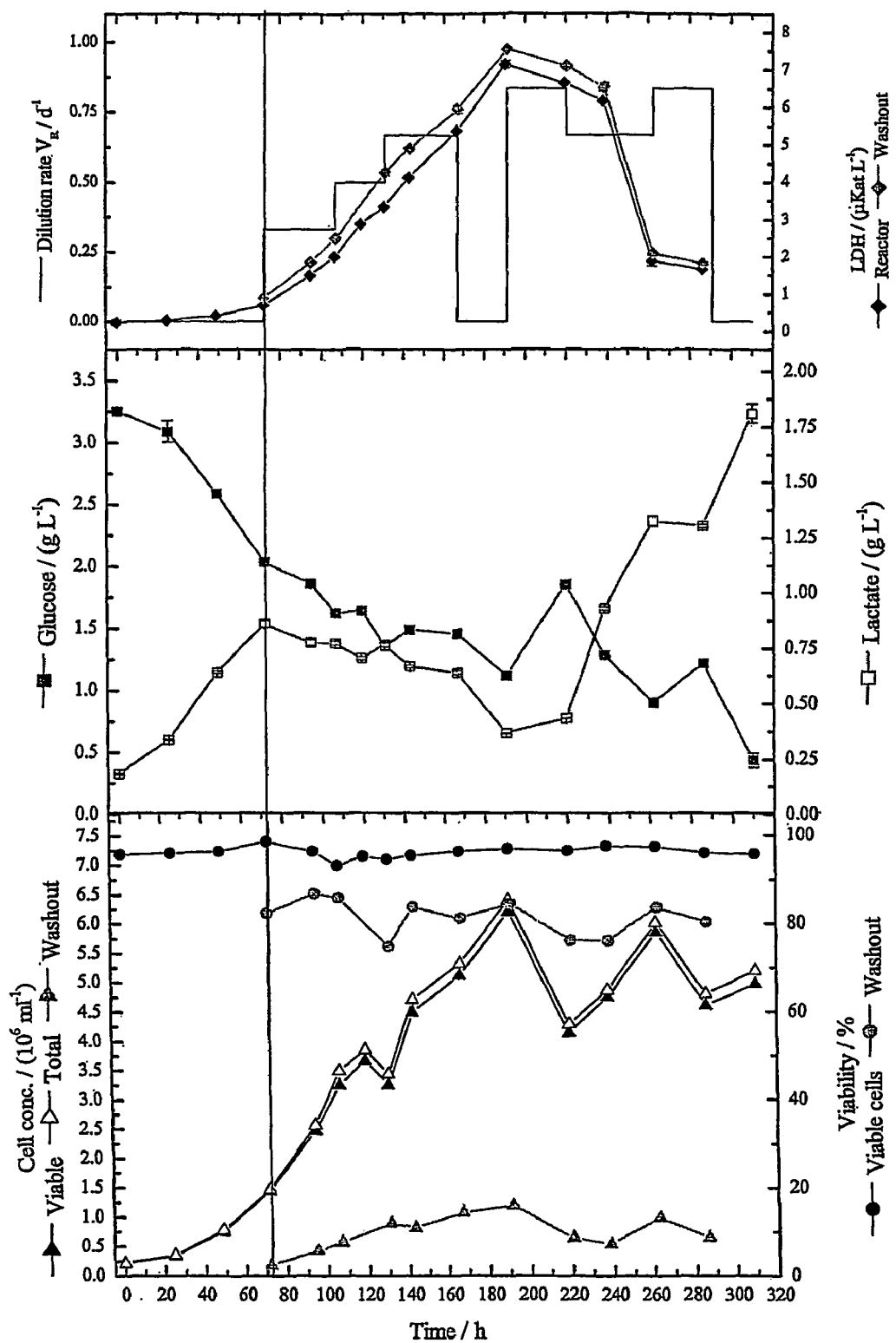
FIG. 5 is an example with a continuous cultivation of NS0 cells in a 5 L reactor by hydrocyclone perfusion in accordance with the present invention.

Examples for the advantages and applications of the present invention are shown in FIGS. 4 and 5.

FIG. 4 shows an example with a continuous cultivation of SP2/0 cells in a 5 L-reactor by hydrocyclone perfusion in accordance with a preferred embodiment according to the present invention. It is apparent that the cell viability was >95% at all times. Cell concentrations of over $8 \times 10^6$ mL$^{-1}$ were obtained at a perfusion rate of 0.5 $V_R d^{-1}$. A ZKTI medium and 8 mM glutamine at a temperature of 37° C. were used.

FIG. 5 shows an example with a continuous cultivation of NS0 cells in 5 L-reactor by hydrocyclone perfusion in accordance with the preferred embodiments of the invention. It is apparent that the cell viability was >95% at all times. High cell concentrations of over $7 \times 10^6$ mL$^{-1}$ were obtained at a perfusion rate of 0.5 $V_R d^{-1}$. CD-hybridoma medium with a mix of cholesterol/lipid and 8 mM glutamine at a temperature of 37° C. were used.

The invention claimed is:

1. A method for separating eukaryotic cells, procaryotic cells, or other biological material which is sensitive to high shearing forces from a suspension, the method comprising the steps of providing at least one hydrocyclone with an inlet and an outlet, the outlet being essentially opposite to the inlet, wherein the interior space of the hydrocyclone converges towards the outlet, delivering the suspension to the inlet of the hydrocyclone, draining off the suspension enriched with the cells or the other material from the outlet, guiding the enriched suspension from or through the outlet by a tube in an essentially acute angle towards the longitudinal axis of the outlet or the longitudinal axis of the hydrocyclone so that the enriched suspension at least close to the outlet has an essentially tangential flow within the tube.

2. A method for separating eukaryotic cells, procaryotic cells, or other biological material which is sensitive to high shearing forces from a suspension, the method comprising the following steps: providing at least one hydrocyclone with an inlet and an outlet, the outlet being essentially opposite to the inlet wherein the interior space of the hydrocyclone converges towards the outlet, delivering the suspension to the inlet of the hydrocyclone, draining off the suspension enriched with the cells or the other material from the outlet; and guiding the enriched suspension from or through the outlet by a tube, which is formed so that at its end opposite to the outlet, the kinetic energy of the enriched suspension is small enough to avoid any damage to the cells or the material of the suspension when it exits the tube.

3. A method for separating eukaryotic cells, procaryotic cells, or other biological material which is sensitive to high shearing forces from a suspension, the method comprising the steps of: providing at least one hydrocyclone with an inlet and an outlet, the outlet being essentially opposite to the inlet wherein the interior space of the hydrocyclone converges towards the outlet, delivering the suspension to the inlet of the hydrocyclone, draining off the suspension enriched with the cells or the other material from the outlet; and guiding the enriched suspension from or through the outlet by a tube so that at its end opposite to the outlet, the flow means transports the enriched suspension below the upper level of a fluid within a bioreactor.

4. A method for separating eukaryotic cells, procaryotic cells, or other biological material which is sensitive to high shearing forces from a suspension, the method comprising the steps of: providing at least one hydrocyclone with an inlet and an outlet, the outlet being essentially opposite to the inlet wherein the interior space of the hydrocyclone converges towards the outlet, delivering the suspension to the inlet of the hydrocyclone, draining off the suspension enriched with the cells or the other material from the outlet; and guiding the enriched suspension from or through the outlet directly below the upper level of a fluid within a bioreactor.

5. The method according to claim 1, wherein the tube is formed so that at its end opposite to the outlet, the kinetic energy of the enriched suspension is small enough to avoid any damage to the cells or the material of the suspension when it exits the tube.

6. The method according to claim 1, wherein the tube is connected to the outlet by an oval-shaped hole in the outlet.

7. The method according to claim 6, wherein the flow means has a length of at least 10 cm.

8. The method according to claim 7, wherein the tube is directed to a bioreactor at its distal end opposite to the outlet of the hydrocyclone.

9. The method according to claim 8, wherein the flow means or a communicating flange of the bioreactor transports the enriched suspension below the upper level of a fluid within the bioreactor.

10. The method according to claim 8, wherein the flow means ends at its distal end opposite to the outlet of the hydrocyclone with preferably acute angle, forming an oval-shaped opening.

11. The method according to claim 10, wherein the distal end of the flow means is arranged in a position, forming preferably an acute angle between the distal end of the flow means and the wall of the bioreactor.

12. A method according to claim 8, comprising separating cells in a perfusion system.

13. A method according to claim 8, wherein at least two hydrocyclones are disposed in parallel to each other.

14. A method according to claim 13, wherein the at least two hydrocyclones drain off by a common flow conduit.

15. An apparatus for separating eukaryotic cells, procaryotic cells, or other biological material which is sensitive to high shearing forces from a suspension, the apparatus comprising: at least one hydrocyclone with an inlet and an outlet, the outlet being essentially opposite to the inlet wherein the interior space of the hydrocyclone converges towards the outlet, an inlet of the hydrocyclone for delivering the suspension into the hydrocyclone, an outlet to drain off the suspension being enriched with cells or the other material, and a tube for guiding the enriched suspension from or through the outlet which is oriented in an essentially acute angle towards the longitudinal axis of the outlet, or the longitudinal axis of the hydrocyclone so that the enriched suspension at least close to the outlet has an essential tangential flow within the tube.

16. An apparatus for separating eukaryotic cells, procaryotic cells, or other biological material which is sensitive to high shearing forces from a suspension, the apparatus comprising: at least one hydrocyclone with an inlet and an outlet, the outlet being essentially opposite to the inlet wherein the interior space of the hydrocyclone converges towards the outlet, an inlet of the hydrocyclone for delivering the suspension into the hydrocyclone, an outlet to drain off the suspension being enriched with cells or the other material; and a tube for guiding the eruiched suspension from or through the outlet, the tube being formed so that at its end opposite to the outlet the kinetic energy of the enriched suspension is small enough to avoid any damage to the cells or the material of the suspension when it is emitted from the tube.

17. An apparatus for separating eukaryotic cells, procaryotic cells, or other biological material which is sensitive to high shearing forces from a suspension, the apparatus comprising: at least one hydrocyclone with an inlet and an outlet, the outlet being essentially opposite to the inlet wherein the interior space of the hydrocyclone converges towards the outlet, an inlet of the hydrocyclone for delivering the suspension into the hydrocyclone, an outlet to drain off the suspension being enriched with cells or the other material; and a tube for guiding the enriched suspension from or through the outlet, the flow means being formed so that at its end opposite to the outlet, the tube transports the enriched suspension below the upper level of a fluid within a bioreactor.

18. An apparatus for separating eukaryotic cells, procaryotic cells, or other biological material which is sensitive to high shearing forces from a suspension, the apparatus comprising: at least one hydrocyclone with an inlet and an outlet, the outlet being essentially opposite to the inlet wherein the interior space of the hydrocyclone converges towards the outlet, an inlet of the hydrocyclone for delivering the suspension into the hydrocyclone, an outlet to drain off the suspension being enriched with cells or the other material, guiding the enriched suspension from or through the outlet directly below the upper level of a fluid within a bioreactor.

19. An apparatus according to claim 15, wherein said tube is formed so that at its end opposite to the outlet, the kinetic energy of the enriched suspension is small enough in order to avoid any damage to the cells or the material of the suspension when it exits the tube.

20. An apparatus according to claim 19, wherein the tube is connected to the outlet by an oval-shaped hole in the outlet.

21. An apparatus according to claim 20, wherein the tube has a length of at least 10 cm.

22. A system comprising a bioreactor and an apparatus according to claim 21 wherein the tube is directed to the bioreactor at its distal end opposite to the outlet of the hydrocyclone.

23. A system according to claim 22, wherein the tube or a communicating flange of the bioreactor transports the enriched suspension below the upper level of a fluid within the bioreactor.

24. A system according to claims 22, wherein the tube ends at its distal end opposite to the outlet of the hydrocyclone with an acute angle, forming an oval-shaped opening.

25. A system according to claim 24, wherein the distal end of the tube is arranged in a position, forming an acute angle between the distal end of the tube and the wall of the bioreactor.

26. A system according to claim 25, wherein the system is used in a perfusion system.

27. A system according to claim 26, wherein there are at least two hydrocyclones disposed in parallel to each other.

28. A system according to claim 27, wherein the at least two hydrocyclones drain off by a common flow conduit.

29. The method of claim 7, wherein the tube has a length of between about 50 to about 100 cm.

30. The apparatus of claim 21, wherein the tube has a length of between about 50 to about 100 cm.

* * * * *